United States Patent [19]
Bailey et al.

[11] Patent Number: 5,605,458
[45] Date of Patent: Feb. 25, 1997

[54] NEGATIVE LOAD FLANK IMPLANT CONNECTOR

[75] Inventors: A. Gregory Bailey, Alabaster; Aubrey C. Folsom, Jr., Pelham, both of Ala.

[73] Assignee: Crystal Medical Technology, a division of Folsom Metal Products, Inc., Birmingham, Ala.

[21] Appl. No.: 398,605

[22] Filed: Mar. 6, 1995

[51] Int. Cl.⁶ ..................................................... A61C 8/00
[52] U.S. Cl. .......................... 433/174; 433/173; 606/73
[58] Field of Search ...................... 433/169, 172, 433/173, 174, 175; 411/309, 307, 310, 311, 411, 414, 415, 426; 285/333, 334; 606/65, 73

[56] References Cited

U.S. PATENT DOCUMENTS

| | | |
|---|---|---|
| 3,579,831 | 5/1971 | Stevens et al. . |
| 3,672,058 | 6/1972 | Nikoghossian . |
| 3,863,344 | 2/1975 | Pillet . |
| 3,955,280 | 5/1976 | Sneer . |
| 3,981,079 | 9/1976 | Lenczycki . |
| 3,989,284 | 11/1976 | Blose ............................... 285/334 |
| 4,016,651 | 4/1977 | Kawahara et al. . |
| 4,229,169 | 10/1980 | Smith et al. ...................... 433/174 |
| 4,318,696 | 3/1982 | Kasama et al. . |
| 4,324,550 | 4/1982 | Reuther et al. ................... 433/174 |
| 4,359,318 | 11/1982 | Gittleman ......................... 433/173 |
| 4,406,623 | 9/1983 | Grafelmann et al. ............. 433/174 |
| 4,568,285 | 2/1986 | Chiaramonte et al. . |
| 4,615,338 | 10/1986 | Ilizarov et al. . |
| 4,631,031 | 12/1986 | Richter ............................. 433/173 |
| 4,653,486 | 3/1987 | Coker . |
| 4,671,768 | 6/1987 | Ton .................................. 433/174 |
| 4,684,555 | 8/1987 | Neumeyer ........................ 428/36 |
| 4,707,001 | 11/1987 | Johnson ........................... 285/332.3 |
| 4,713,004 | 12/1987 | Linkow et al. ................... 433/174 |
| 4,826,434 | 5/1989 | Krueger ............................ 433/174 |
| 4,881,897 | 11/1989 | Franek et al. .................... 433/169 |
| 4,938,694 | 7/1990 | Ledermann ...................... 433/173 |
| 5,000,686 | 3/1991 | Lazzara et al. ................... 433/174 |
| 5,007,835 | 4/1991 | Valen ................................ 433/174 |
| 5,022,860 | 6/1991 | Lazzara et al. ................... 433/173 |
| 5,026,280 | 6/1991 | Dürr et al. . |
| 5,040,982 | 8/1991 | Stefan-Degar . |
| 5,061,181 | 10/1991 | Niznick ............................ 433/174 |
| 5,078,607 | 1/1992 | Niznick ............................ 433/174 |
| 5,092,635 | 3/1992 | Debange et al. ................. 285/334 |
| 5,114,343 | 5/1992 | Musikanti et al. . |
| 5,133,662 | 7/1992 | Metcalfe . |
| 5,174,755 | 12/1992 | Fukuda ............................. 433/173 |
| 5,195,892 | 3/1993 | Gersberg .......................... 433/174 |
| 5,199,873 | 4/1993 | Schulte et al. ................... 433/174 |
| 5,234,430 | 8/1993 | Huebner ........................... 606/60 |
| 5,238,405 | 8/1993 | Marlin .............................. 433/173 |
| 5,246,369 | 9/1993 | Poulmaire ........................ 433/173 |
| 5,259,398 | 11/1993 | Vrespa ............................. 128/898 |
| 5,269,686 | 12/1993 | James ............................... 433/174 |
| 5,415,442 | 5/1995 | Klementich ...................... 285/334 |
| 5,419,595 | 5/1995 | Yamamoto et al. .............. 285/334 |

FOREIGN PATENT DOCUMENTS

| | | | |
|---|---|---|---|
| 3018329 | 9/1993 | WIPO | ..................... 285/334 |

*Primary Examiner*—Cary E. O'Connor
*Attorney, Agent, or Firm*—Veal & Associates

[57] ABSTRACT

An improved thread profile for use in medical implants utilizes a negative to slightly positive load flank inclination to minimize radial separation of the threaded connection by increasing the radial force required to overcome the surface and interference resistance to relative motion between the made-up abutting load faces of the connector threads.

11 Claims, 4 Drawing Sheets

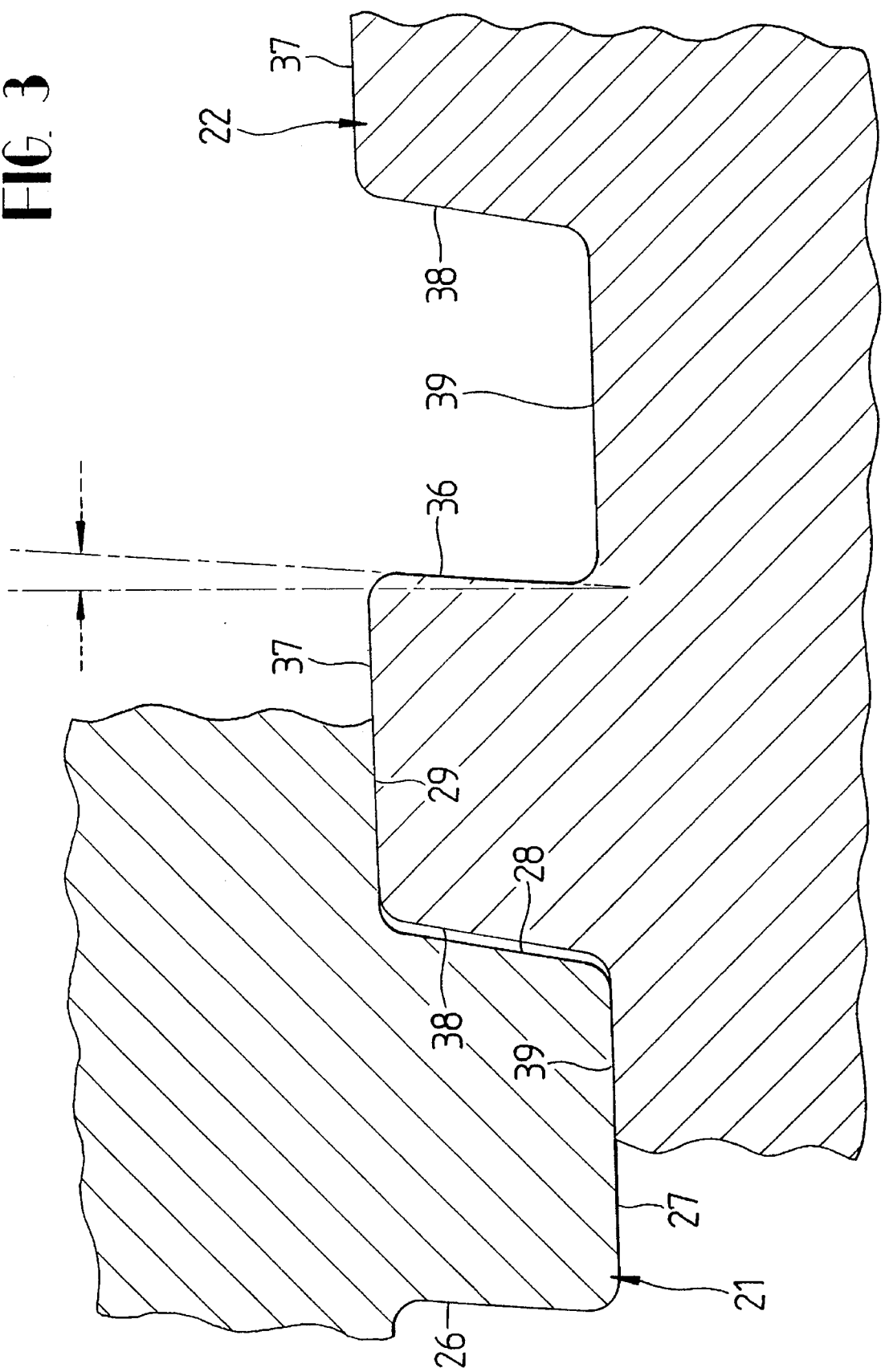

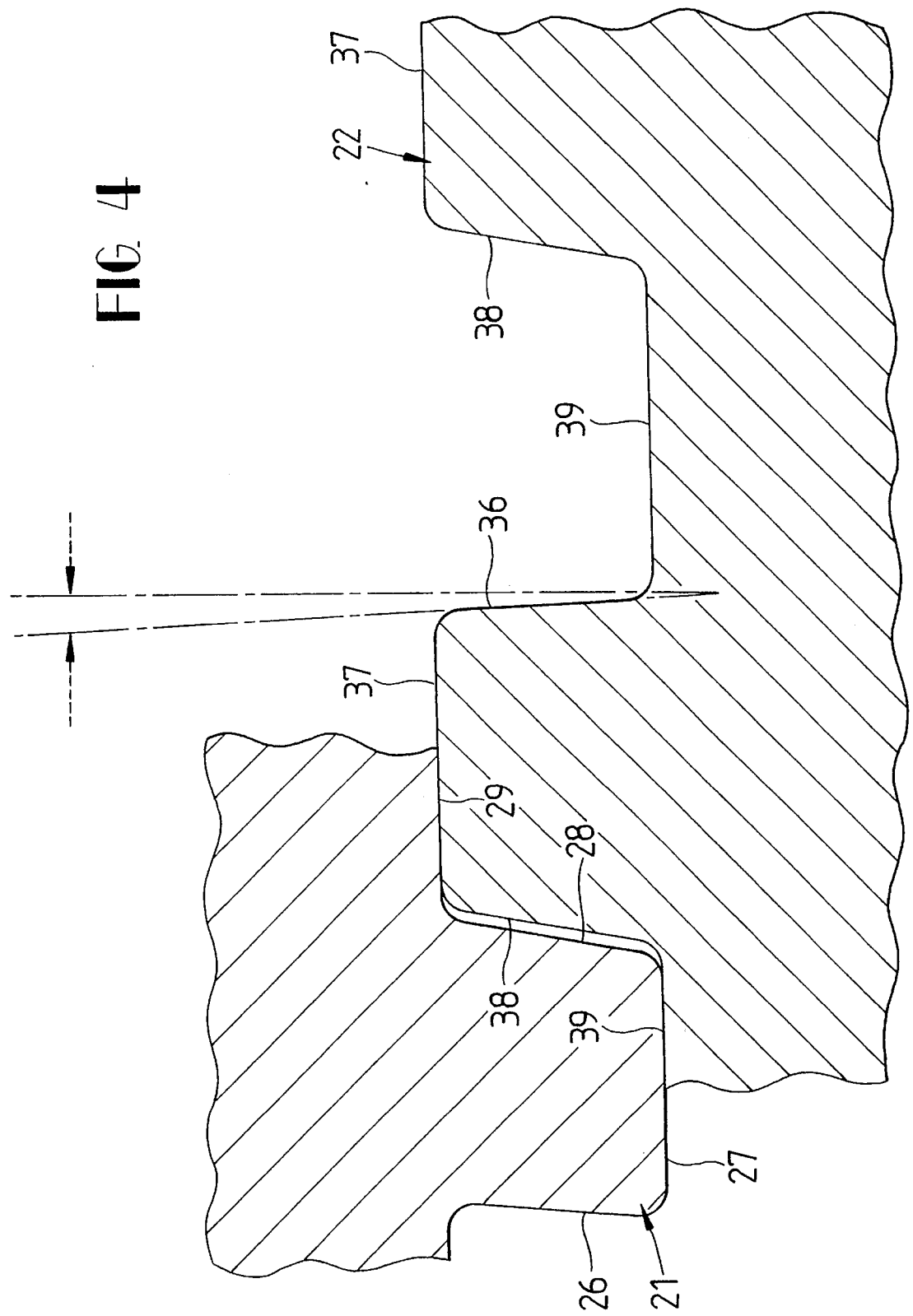

NEGATIVE LOAD FLANK IMPLANT CONNECTOR

FIELD OF THE INVENTION

The present invention relates to prosthetic implantation of devices which are osseointegrated into bone. In more particularity, the present invention relates to the field of connectors used in such implants that secure the prosthesis to the implanted portion of the device. The present invention relates to the design of the thread profile so as to maximize the effectiveness of the connection within the implant/prosthesis assembly.

BACKGROUND

The prior art of implants extends back, at least, into the last century; however, only in the last twenty-five years have implants such as hip replacements, knee replacements and dental implants been widely used. These devices often employ threaded connections to fasten components of the prosthetic assembly together. Reported common problems noted by practitioners are breakage of the screw and loosening of the screw fixating the prosthesis (see U.S. Pat. No. 5,213,500, for example). It is believed that one cause of the failure of the threaded connection is the stress imposed on selected threads along the connection. A nominally manufactured component can place portions of the threads in stress conditions above the yield strength of the material, resulting in permanent deformation of the thread. This yielding may lead to a loss of pre-load tension in the connection, leading to relative motion between the joined components, and compromising the function of the prosthesis. Likewise, dynamic fatigue of the overloaded fastener can lead to catastrophic failure. These stress concentrations are compounded by the physical size restraints placed on prosthetic components. The materials which are available to the designer to choose from, to wit,—polymers, metals, and composites—oftentimes exhibit creep characteristics. The stress-raising factors encountered in implants aggravate the tendency of these materials to have time-dependent strain at stress levels below yield.

Stress placed on connectors may be radial or longitudinal and may lead to radial separation of the connector surface with attendant loss of stability in the prosthesis.

SUMMARY OF THE INVENTION

It is the principal object of the present invention to enhance the stability of the components in medical implants such as are used in dental and orthopedic procedures.

Another object of the invention is to reduce radial separation of threaded connector surfaces used in medical implants which are subjected to dynamic loading to reduce the loss of stability of such implants.

Yet another object of the invention is to reduce the incidence of replacements of medical implants due to loosening of the implant connection.

The forgoing objects are accomplished by recognizing that hoop type strain placed on the female receptacle in relatively thin walled connections can cause the female receptacle to yield radially in some regions of the connection. In as much as there is little that can be done to increase the wall thickness to resist the radial expansion or movement, the internal structure of the threaded connection must be altered. In the present invention this is accomplished by a thread design that elevates the radial force component needed to induce radial movement by increasing the interference along the load flank in relation to radial motion. That is to say, in conventional threaded connections the stress applied by torquing the connected members has a longitudinal component that places the connection in tension and compression and a transverse component generated by the wedging action of the opposing load flanks which urges the connected members opposite each other. The present invention recognizes that past medical implants have virtually all used conventional threads and thus have encountered the difficulty; accordingly, the present design intends to resolve the force components differently such that abutting load flanks will have equally compressive radial force components, thus improving the holding capacity of such necessarily small connectors. The present invention requires the thread profile to include a load flank which has an inclination near normal relative to the axis of the connection. In the profile of the thread utilized in this invention near normal mean a positive inclination of 5 degrees or less and includes a negative inclination. It will be appreciated that a 15 degree or less positive inclination will not generate substantial radially separating wedging action as the connection is made up and will provide a relatively large surface contact area under tension to resist radially separating forces. That is to say, pre-load forces applied will be closer to normal to the load flank of the thread and the separation force will be closer to parallel, thus disregarding the force needed to deform the receptacle, it can be seen that a force equal to or greater than the surface to surface resistance to separation under the pre-load conditions will decrease as the angle increases above 5 degrees because the surface to surface resistance is lessened.

In embodiments wherein the load flank is actually negative, the separation forces are more dependent on the interference at the surfaces in as much as the load flank of the male thread overlies the load flank of the female thread, such that outward movement of the female receptacle can only occur if the male thread is distorted by the separation force such the surface is actually changed by the relative radial movement of the mating threads.

BRIEF DESCRIPTION OF THE DRAWINGS

The connector embodying features of our invention are depicted in the accompanying drawings which form a portion of this disclosure and wherein:

FIG. 3 is a sectional view along the longitudinal axis of the connection showing the turns on one side of the connection; and FIG. 4 is a sectional view long the longitudinal axis showing the turns in a slightly positive load flank embodiment.

DESCRIPTION OF THE PREFERRED EMBODIMENT

Figure 1:
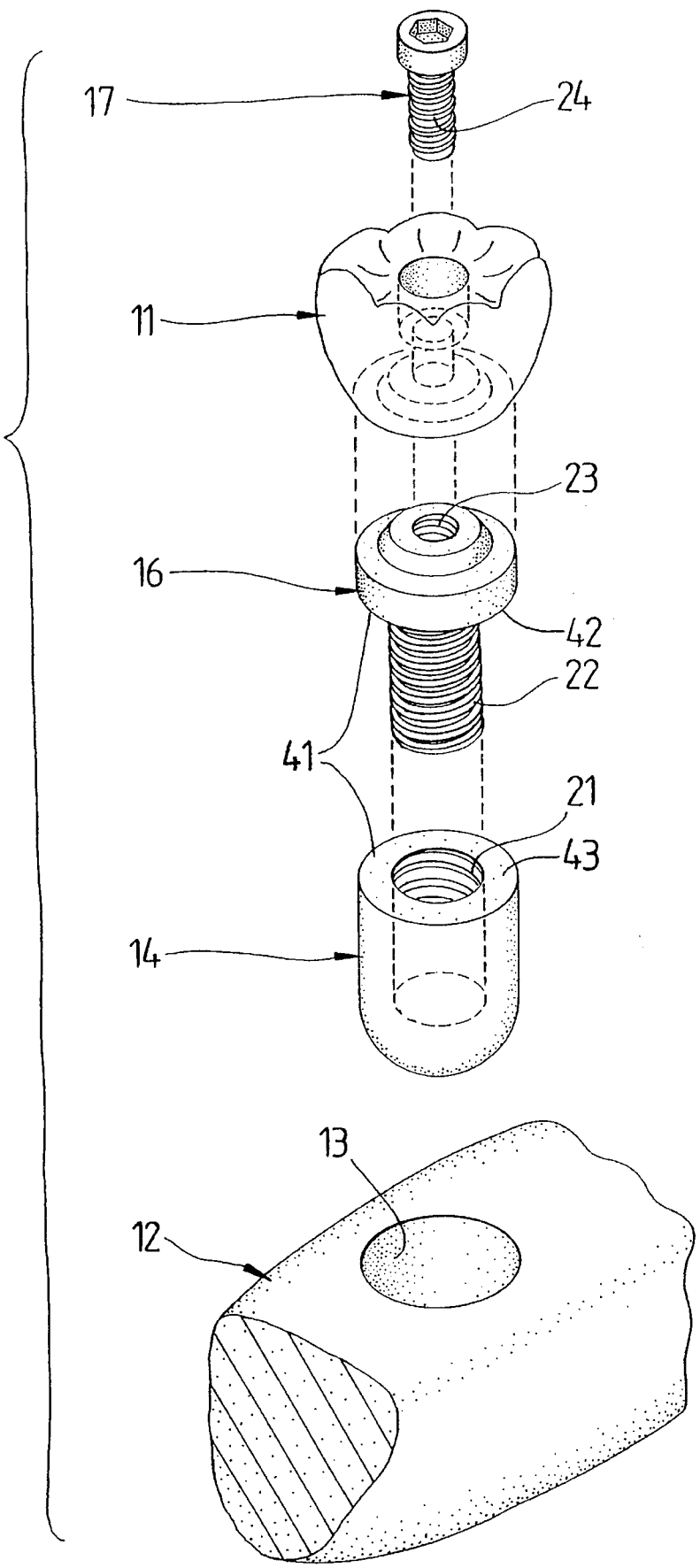
FIG. 1 is an exploded perspective view of a dental implant using our connector.

Referring to the drawings for a clearer understanding of the invention it may be seen in FIG. 1 that the invention is adapted for use in the field of dental implants, wherein a prosthesis such as a tooth 11 or bridge (not shown) is to be attached to the underlying bone 12. As will be appreciated from the prior art, the surgeon prepares a socket 13 in the bone and positions the implant fixture 14 within the bone 12.

The present invention is not directed to the attachment of the fixture 14 to the bone; therefore, the external configuration as shown is not intended to depict any particular implant, however the invention is directed to the interaction of the implant 14 with an abutment 16 received therein and the interaction of the abutment 16 with a screw 17 used to attach the prosthesis 11 to the abutment 16.

As may be seen more clearly in FIG. 3, the present invention is directed specifically to the formation and interaction of the threaded connection between the components. Implant 14 has a female thread 21 which cooperatively engages the male thread 22 of the abutment 16. Likewise, abutment 16 has a threaded axial bore wherein female threads 23 are positioned to engage the male thread 24 of screw 17. It will be noted that the profile of the thread is a modified truncated thread wherein the female thread profile includes a load flank 26 intersecting a crest 27, a stab flank 28 extending from the crest 27 to a root 29 such that the turns, hereinafter referred to as the threads, of the thread along the length of the fastener sequentially repeat the profile with the crest defining the inner diameter of the thread and the root the outer diameter. Likewise, the male thread profile includes a load flank 36 intersecting a crest 37; a stab flank 38 extending from the crest 37 to a root 39 such that the threads along the length of the fastener sequentially repeat the profile with the crest defining the outer diameter of the thread and the root the inner diameter. The thrust connection 41 is usually the abutting portion of the connector which prevents further longitudinal relative movement of the connector components. For example the abutment 16 may have a shoulder 42 which is urged into contact with the implant surface 43. It will be appreciated that tightening the connector loads the connection by placing the screw or bolt under tension between the thrust connection and the load flank interface. If the male thread profile and female thread profile are not properly matched the connection will not remain secure. Further, dynamic loading such as by chewing in a dental implant or movement in an orthopedic implant will also load the connector.

Figure 2:
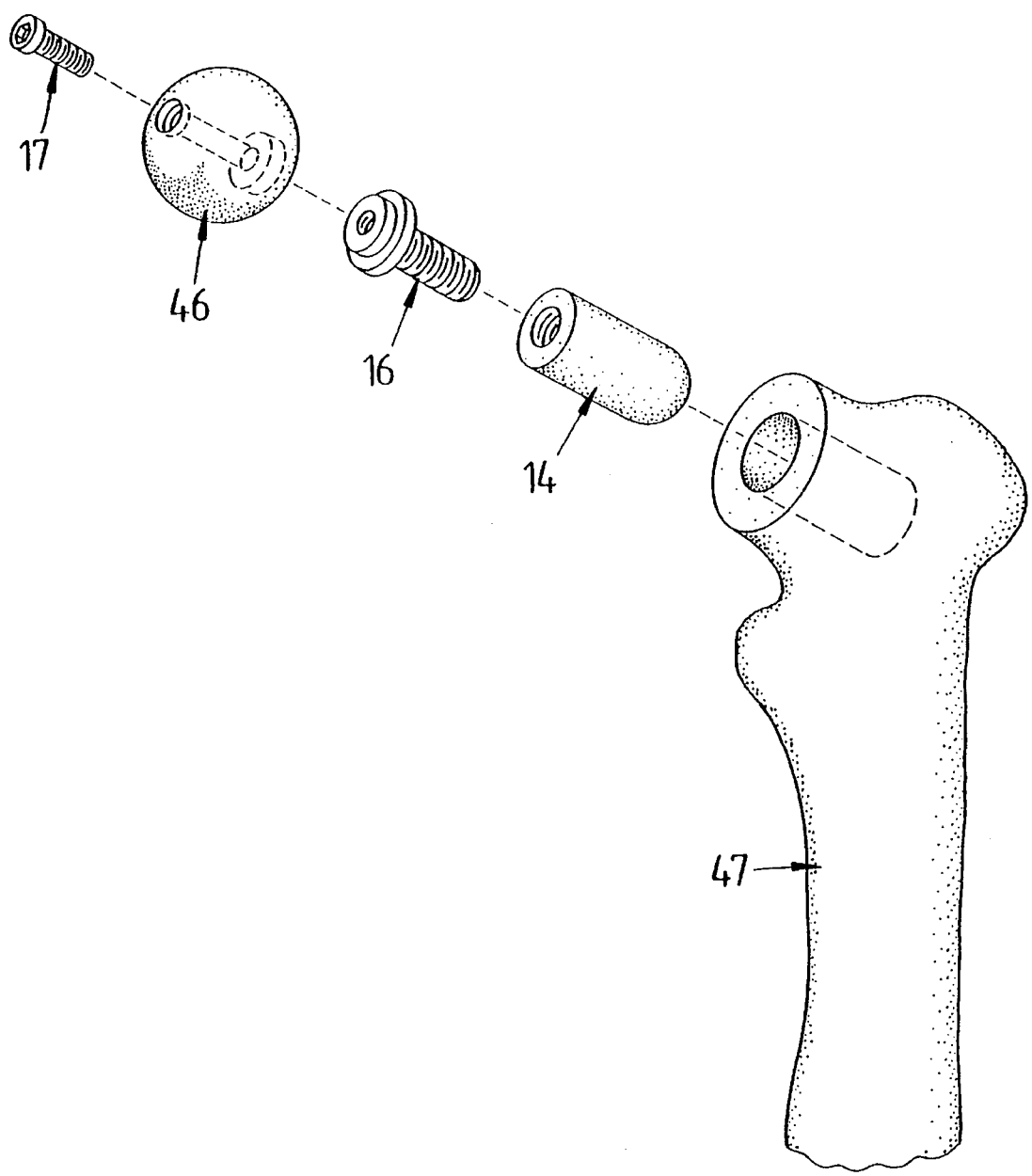
FIG. 2 is a perspective view of a orthopedic implants using our connector.

It is further contemplated that the present invention may be used in implants other than dental implants—specifically, orthopedic implants. One possibility for use of the present invention is to permit the interimplant connection of members such that certain parts of the implant could be made modular for standardization rather than unitary. For example, if a socket were to be aligned in a specific plane of the hip or a ball placed within a socket at a joint, an implant stem affixed to ball or socket using the present invention would enable the surgeon to mate the ball and socket, and select a stem of appropriate size and length for a particular patient from a set of standard stems and modular and ball or socket units. As seen in FIG. 2, a ball 46 is affixed to a bone 47 by means of implant 14, abutment 16, and screw 17.

Referring particularly to FIG. 3, it may be seen that the female receptacle utilizing our invention has a negative load flank 26 such that the load flank adjacent the crest of the thread is closer to the thrust connection 41 than the same load flank 26 adjacent the root of the thread. The male thread load flank 36 is complementary. Thus, at the minor diameter of abutting load flanks 26 and 36 when made up under pre-load stress, a plane normal to the connection axis passes through the male tread 36 such that a portion of the material forming the thread radially overlies the female load flank. Accordingly, radial outward movement of the female thread would require displacement the interstial portion of the male thread in the angle between the female load flank and root, such that an interference condition would occur. It may be seen that the forces required to overcome the interference will be dictated by the mallablitiy of the material selected and the volume of material involved such that this type thread profile significantly increases the resistance of the connection to radial separation forces.

FIG. 4 depicts the invention in an embodiment wherein the abutting load flanks are inclined at a slight positive angle of less than 15 degrees. As may be appreciated, there is no overlying portion of the other thread preventing radial movement of the load flank; however, the radial force is applied nearly along the interface and the tension forces are nearly perpendicular thereto, such that large metal to metal surface resistance must be over come to achieve radial movement. Accordingly, in applications where the negative load flank may be impractical or impossible due to the small size the implant fastener or other constraint, the positive load flank may be used with enhanced success over the standard thread.

While we have shown our invention in one form, it will be obvious to those skilled in the art that it is not so limited but is susceptible of various changes and modifications without departing from the spirit thereof.

What we claim is:

1. A medical implant assembly having an improved thread profile for use in implant connectors, wherein a threaded member is used to attach components of the implant and is threadably engaged by a cooperatively formed threaded receptacle, said thread profile including a stab flank and a load flank separated by a crest with successive turns of said thread about a longitudinal axis being separated by a root, wherein said load flank has an inclination between positive 5 degrees relative to a plane normal to the longitudinal axis and a negative inclination.

2. An assembly as defined in claim 1 wherein said load flank extends partially over said root.

3. An assembly as defined in claim 1 formed on a cooperative threaded member and a cooperative threaded receptacle therefor such that the load flank of said threaded member overlies the load flank of said receptacle when said receptacle and member are engaged such that torquing stress on said receptacle tending to exert hoop stress on said receptacle cause the load flank of said of the receptacle to be urged against the load flank of said threaded member.

4. An assembly as defined in claim 1 wherein said load flank is inclined negatively relative to a plane normal to said longitudinal axis.

5. An improvement in medical implant connections wherein an implant assembly uses an implant secured within a cavity formed within a bone of a patient, said implant forming a threaded receptacle, an abutment having an external thread cooperatively formed for engagement with said implant and an internal thread, a fastener having an external thread cooperatively formed for engagement with the internal thread of said abutment for fastening a prosthesis to said abutment, wherein the improvement comprises a thread profile for at least one set of cooperatively formed threads comprising a stab flank and load flank separated by a crest, wherein successive turns of said thread along a longitudinal axis are separated by a root, and where in the load flank of said thread profile is inclined between a negative inclination relative to a plane normal to said longitudinal axis and a positive inclination of less than 5 degrees relative to said plane.

6. The improvement as defined in claim 5 wherein said load flank is inclined at a negative angle of less than 30 degrees relative to said plane.

7. The improvement as defined in claim 5 wherein the load flank formed on said threaded member is urged into radially abutting relationship with the cooperative load flank of said threaded receptacle and retards radial expansion of said threaded receptacle under torque.

8. An improvement in dental and orthopedic implant connections wherein an implant has at least two members held in abutment by a threaded union, each member having a cooperative thread profile including a load flank and stab flank separated by a crest with the thread forming turns about a longitudinal axis through said union forming a root between the adjacent stab and load flanks, wherein the load flanks of each thread abut in interfering relationship with each load flank having an inclination ranging from a negative angular measure to less than 10 degrees relative to a plane normal to said axis.

9. The improvement as defined in claim 8 wherein at least one of said members is attached to a bone.

10. The improvement as defined in claim 8 wherein said abutting load flanks are inclined at a negative angle such that each of said load flanks oppose radial movement toward each other.

11. The improvement as defined in claim 8 wherein said implant assembly includes a prosthesis which is secured to said assembly by said connection.

\* \* \* \* \*